(12) United States Patent
Zander et al.

(10) Patent No.: US 11,103,294 B2
(45) Date of Patent: Aug. 31, 2021

(54) BONE SCREW SYSTEM

(71) Applicant: Stryker European Operations Holdings LLC, Kalamazoo, MI (US)

(72) Inventors: Nils Zander, Eckernförde (DE); Claudia Wolter, Kiel (DE)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 0 days.

(21) Appl. No.: 16/307,327

(22) PCT Filed: Jun. 9, 2016

(86) PCT No.: PCT/US2016/036655
§ 371 (c)(1),
(2) Date: Dec. 5, 2018

(87) PCT Pub. No.: WO2017/213653
PCT Pub. Date: Dec. 14, 2017

(65) Prior Publication Data
US 2019/0133661 A1 May 9, 2019

(51) Int. Cl.
*A61B 17/86* (2006.01)

(52) U.S. Cl.
CPC ...... *A61B 17/8695* (2013.01); *A61B 17/8605* (2013.01); *A61B 17/863* (2013.01); *A61B 2017/8655* (2013.01)

(58) Field of Classification Search
CPC ............ A61B 17/8695; A61B 17/8004; A61B 17/8009; A61B 17/8019; A61B 17/8028;
(Continued)

(56) References Cited

U.S. PATENT DOCUMENTS 4,988,351 A   1/1991   Paulos et al.
5,041,113 A   8/1991   Biedermann et al.
(Continued)

FOREIGN PATENT DOCUMENTS

WO   8803781 A1   6/1988
WO   2014142823 A1   9/2014

OTHER PUBLICATIONS

International Search Report for International Application No. PCT/US2016/036655 dated Sep. 8, 2016.
(Continued)

*Primary Examiner* — Matthew J Lawson
*Assistant Examiner* — Lisa Nguyen
(74) *Attorney, Agent, or Firm* — Lerner, David, Littenberg, Krumholz & Mentlik, LLP

(57) ABSTRACT

The invention relates to a bone screw system, an implant system and a method of locking a bone screw system into a bore. The bone screw system comprises a bone screw and a washer. The screw comprises a screw head and a screw shaft. The washer comprises a washer bore. A diameter of the washer bore is larger than an outer diameter of the screw shaft. This allows a displacement of the screw shaft within the washer bore. The diameter of the washer bore is smaller than an outer diameter of the screw head. This prevents the screw head from moving through the washer bore. The screw and the washer comprise each an engagement portion for an engagement with each other. At least one of these engagement portions comprises an inclined surface. The inclined surface is configured to force the screw shaft sideward upon screwing in of the screw so that a longitudinal axis of the screw is tilted relative to the axis of the washer bore.

20 Claims, 2 Drawing Sheets

(58) Field of Classification Search
CPC .......... A61B 17/8033; A61B 17/7233; A61B 17/746; A61B 17/725; A61B 17/7241
See application file for complete search history.

(56) References Cited

U.S. PATENT DOCUMENTS

| | | | |
|---|---|---|---|
| 8,361,127 B2 | | 1/2013 | Biedermann et al. |
| 8,632,545 B2 | * | 1/2014 | Sarangapani ...... A61B 17/8057 606/280 |
| 8,992,585 B2 | | 3/2015 | Patterson et al. |
| 2003/0083660 A1 | * | 5/2003 | Orbay ................ A61B 17/68 606/281 |
| 2004/0158252 A1 | | 8/2004 | Prager et al. |
| 2005/0165400 A1 | | 7/2005 | Fernandez |
| 2008/0306555 A1 | | 12/2008 | Patterson et al. |
| 2009/0062862 A1 | * | 3/2009 | Perrow ............ A61B 17/8891 606/280 |
| 2009/0192551 A1 | * | 7/2009 | Cianfrani ............ A61B 17/685 606/301 |
| 2010/0094356 A1 | | 4/2010 | Varela et al. |
| 2012/0065690 A1 | * | 3/2012 | Perrow ............ A61B 17/8047 606/294 |
| 2012/0123484 A1 | * | 5/2012 | Lietz .................. A61B 17/151 606/281 |
| 2014/0249587 A1 | * | 9/2014 | Cawley ............ A61B 17/8047 606/291 |

OTHER PUBLICATIONS

Extended European Search Report for Application No. 16904802.2 dated Dec. 4, 2019, 8 pages.

* cited by examiner

BONE SCREW SYSTEM

CROSS-REFERENCE TO RELATED APPLICATIONS

The present application is a national phase entry under 35 U.S.C. § 371 of International Application No. PCT/US2016/036655, filed Jun. 9, 2016, the disclosure of which is incorporated herein by reference in its entirety.

BACKGROUND OF THE INVENTION

The invention relates to a bone screw system, an implant system and a method for locking a bone screw system into a bore. The bore can be provided in e.g. an implant, a plate, a nail or the like.

Angular stable locking of implants, plates, nails or the like is associated with positive impact on fracture healing. US 2004/0158252 A1 discloses an implant for osteosynthesis, such as, for example, a bone nail, with an implant body which has at least one bore with a threaded portion and a bone screw which engages the thread when it is threaded into a bone for the fixation of the implant body. The threaded bore has an annular groove the diameter of which is larger than the thread outer diameter, and which receives a ring of a deformable material with an inner diameter, which is larger than the outer diameter of the thread of the bone screw so that the ring extends partially into the bore.

Various designs to increase the fragment stability are commercially available. These solutions are based on modification of the locking holes (e.g. an internal thread) and/or complex technical solutions including altered operative techniques with additional implant components.

However, the mentioned concepts suffer from their respective technical complexity, the required costly implant, plate or nail modification by e.g. additional threads, and a missing backward compatibility to existing implants, plates, nails or the like.

BRIEF SUMMARY OF THE INVENTION

Hence, there may be a need to provide an improved bone screw system, which is in particular less complex compared to prior art systems.

The problem of the present invention is solved by the subject-matters of the independent claims, wherein further embodiments are incorporated in the dependent claims. It should be noted that the aspects of the invention described in the following apply also to the bone screw system and the method for locking a bone screw system into a bore.

According to the present invention, a bone screw system is presented. The bone screw system can be used for angularly locking a bone screw into a bore. The screw may be a standard bone screw. The bore can be provided in e.g. an implant, a plate, a nail, an intramedullary nail, a rod, a pin and the like. The bore may be a circular hole, a longitudinal groove or may have any other shape. The wall of the bore may not be provided with a thread and may therefore be straight and smooth. As a result, the bone screw system can be used for interlocking a screw and a bore of arbitrary shape in e.g. an implant, a plate, a nail or the like.

The bone screw system comprises a bone screw and a washer. The screw comprises a screw head and a screw shaft. The washer comprises a washer bore. A diameter of the washer bore is larger than an outer diameter of the screw shaft. This size difference is larger than necessary for a simple longitudinal passage of the screw shaft through the washer bore. This allows a sideward or lateral displacement and not only a longitudinal displacement of the screw shaft within the washer bore. In an example, the diameter of the washer bore is more than 10 percent larger than the outer diameter of the screw shaft. Further, the diameter of the washer bore is smaller than an outer diameter of the screw head. This prevents the screw head from moving through the washer bore.

The screw and the washer comprise each an engagement portion for an engagement with each other. At least one of these engagement portions comprises an inclined surface or chamfered geometry. The inclined surface is configured to force the screw shaft sideward upon screwing in of the screw into the washer bore so that a longitudinal axis of the screw is tilted relative to a longitudinal axis of the washer bore. The longitudinal axis of the washer bore may be parallel to a longitudinal axis of the bore in the implant, plate, nail or the like. The axes of the washer bore and of the bore in the implant, plate, nail or the like may be the same or displaced to each other.

In other words, the screw and/or the washer comprise an inclined surface configured to force the screw shaft sideward upon screwing in of the screw into the washer bore. The sideward movement of the screw shaft leads to a tilt of the longitudinal screw axis and thereby of the screw relative to the washer bore axis. In other words, the screw is inserted at a slight angle into the washer bore and thereby provides a controlled angular deviation or offset between the screw axis and the washer bore axis. By this tilt, angle, deviation or offset, the screw may be locked into or be interlocked with the bore in e.g. the implant.

The bone screw system according to the invention may provide reduced technical complexity and reduced costs compared to prior art systems. The reason may be that no modifications of the washer bore are necessary. For example, no threads in the washer bore are necessary. Also a backward compatibility to existing implants, plates, nails or the like is provided. Further, conventional mass produced screws may be used.

Due to the slightly angled insertion of the screw, the bone screw system according to the invention may further provide a significantly decreased clearance and an increased, in particular axial stiffness and stability compared to prior art systems. The increased stiffness provided by the bone screw system according to the invention may lead to an in particular angular stable locking of implants, plates, nails or the like. The improved angular stable locking of implants may be associated with a positive impact on fracture healing. This is true especially for inherently unstable fracture situations in combination but not limited to short shaft fragments, wide intramedullary canals, poor bone qualities, and/or "distal" (opposite end to the targeting device adaptation) locking configurations like in the treatment of distal tibia fractures.

In case the bore is not drilled perpendicular to a surface of e.g. the implant, the tilting of the screw according to the present invention can also be used to tilt the screw in a direction perpendicular to the implant surface.

In an example, the diameter of the washer bore is more than 10 percent larger than the outer diameter of the screw shaft. In an example, the diameter of the washer bore is more than 20 percent larger than the outer diameter of the screw shaft. In an example, the diameter of the washer bore is more than 30 percent larger than the outer diameter of the screw shaft.

As stated above, the screw and the washer comprise engagement portions for an engagement with each other.

The engagement portions may comprise a straight or curved surface and an inclined surface, whereby one is arranged at the screw and the other at the washer bore or vice versa. The engagement portions may also comprise two inclined surfaces, so that both, the screw and the washer bore, are each provided with an inclined surface. In an example, at least one of the engagement portions is cone shaped. The inclined surface is configured to force the screw shaft sideward upon screwing in of the screw into the washer bore so that a longitudinal axis of the screw is tilted relative to the axis of the washer bore.

In an example, the engagement portion of the screw is arranged as a transition between the screw shaft and the screw head. In an example, the engagement portion of the screw comprises an outer surface of a proximal shaft portion of the screw.

In an example, the engagement portion of the washer comprises an inner surface of the washer bore.

In an example, the washer comprises a fixing mechanism at a bottom surface of the washer. The fixing mechanism may be configured for an engagement with a surface provided below the washer bore and the implant bore as e.g. a bone surface. In other words, the fixing mechanism may firmly anchor the washer and thereby the bone screw system to e.g. a near cortex of the bone. This can in particular be done before a final seating of the screw and thereby of the entire bone screw system. After the final seating of the screw, the bone screw system may be held to the bone surface by means of the screw and the fixing mechanism.

In an example, the fixing mechanism comprises at least a spike at the bottom surface of the washer, wherein the spike is configured for an engagement with the bone surface. In an example, the fixing mechanism comprises a plurality of spikes at the bottom surface of the washer, wherein the spikes are configured for an engagement with the bone surface.

According to the present invention, also an implant system for locking a bone screw system into a bore of e.g. an implant is presented. The implant system comprises a bone screw system as described above and an implant. The implant is configured to be fixed to a bone by means of the screw system.

According to the present invention, also a method for locking a bone screw system into a bore of e.g. an implant is presented. The method of locking a bone screw system into a bore comprises the following steps:
 a) providing a screw system as described above,
 b) inserting a screw of the screw system into a washer bore of a washer of the screw system,
 c) screwing the screw with a longitudinal screw axis into the washer bore with a longitudinal washer bore axis, wherein a distal shaft portion of the screw is aligned with the washer bore axis, and
 d) engaging engagement portions of the screw and the washer. At least one of the engagement portions comprise an inclined surface so as to force the screw sideward upon further screwing in of the screw so that the screw axis is tilted relative to the washer bore axis.

In an example, the washer is placed on the bore in e.g. a bone or in an implant provided on the bone. In an example, the screw is screwed into bone or into the implant mounted on or in the bone. In an example, an inner edge of the washer bore may be aligned with an inner edge of the bore. Thus, a central axis of the larger bore of the washer may be offset from a central axis of the bore in the bone or in the implant. A diameter of the washer bore may be more than 20 percent larger than an outer diameter of the screw shaft. The washer may be provided with spikes which fix the washer at the bore. Then, the screw is screwed in the fixed washer. When a head of the screw slides down an inclined surface of the washer, the screw tilts. A user could thereby align an offset between the washer bore and the implant or bone bore depending on how he/she wants the screw to tilt. It shall be understood that the bone screw system and the method for locking a bone screw system into a bore according to the independent claims have similar and/or identical preferred embodiments, in particular, as defined in the dependent claims. It shall be understood further that a preferred embodiment of the invention can also be any combination of the dependent claims with the respective independent claim. These and other aspects of the present invention will become apparent from and be elucidated with reference to the embodiments described hereinafter.

These aspects of the invention may be achieved by a bone screw system comprising a screw, and a washer. The screw comprises a screw head and a screw shaft, wherein the washer comprises a washer bore with a diameter being larger than an outer diameter of the screw shaft allowing a sideward displacement of the screw shaft within the washer bore. The bore being smaller than an outer diameter of the screw head preventing the screw head from moving through the washer bore.

The screw and the washer comprise engagement portions for an engagement with each other, and wherein at least one of the engagement portions comprise an inclined surface so as to force the screw shaft sideward upon screwing in of the screw so that a longitudinal axis (A) of the screw is tilted relative to a longitudinal axis (B) of the washer bore. The diameter of the washer bore is preferably more than 10 percent larger than the outer diameter of the screw shaft. The diameter of the washer bore may be more than 20 percent larger than the outer diameter of the screw shaft. The diameter of the washer bore may be more more than 30 percent larger than the outer diameter of the screw shaft.

The engagement portion of the screw may be arranged as a transition between the screw shaft and the screw head. The engagement portion of the screw may comprise an outer surface of a proximal shaft portion of the screw and wherein the engagement portion of the washer may comprise an inner surface of the washer bore. At least one of the engagement portions may be conically shaped. The washer may comprise a fixing mechanism on a bottom surface configured for an engagement with a bone surface. The implant system may further comprise an implant, wherein the implant is configured to be fixed to a bone by means of the screw system.

The aspects may be achieved by a method for locking a bone screw system, comprising the following steps: providing a bone screw system comprising a screw, and a washer as described above, inserting the screw of the bone screw system into the washer of the bone screw system, screwing the screw into bone with a longitudinal screw axis (A) into the washer bore with a longitudinal washer bore axis (B), wherein a distal shaft portion the screw is aligned with the washer bore axis (B), and engaging engagement portions of the screw and the washer, wherein at least one of the engagement portions comprise an inclined surface so as to force the screw sideward upon further screwing in of the screw so that the longitudinal screw axis (A) is tilted relative to the washer bore axis (B).

An outer surface of the screw may be aligned with an inner edge of the washer bore prior to screwing the screw into the washer bore. A diameter of the washer bore may preferably be more than 20 percent larger than an outer diameter of the screw shaft. The screw may be screwed into bone or into an implant mounted on or in the bone such as, for example, a bone plate. The washer is placed on a bone and preferably held in a fixed position on the bone while the bone screw is screwed into the bone. The washer preferably has a bone contacting surface comprising spikes for engaging the bone and fixing the washer in a position on the bone.

The engagement portion on the screw may be a part-spherical surface on the head of the screw and the engagement portion on the washer may be a conical recess around the bore in the washer with inclined surfaces extending inwardly towards a central axis of the washer bore on moving towards the washer bottom bone contacting surface.

BRIEF DESCRIPTION OF THE DRAWINGS

Exemplary embodiments of the invention will be described in the following with reference to the accompanying drawings.

DETAILED DESCRIPTION

Figure 1:
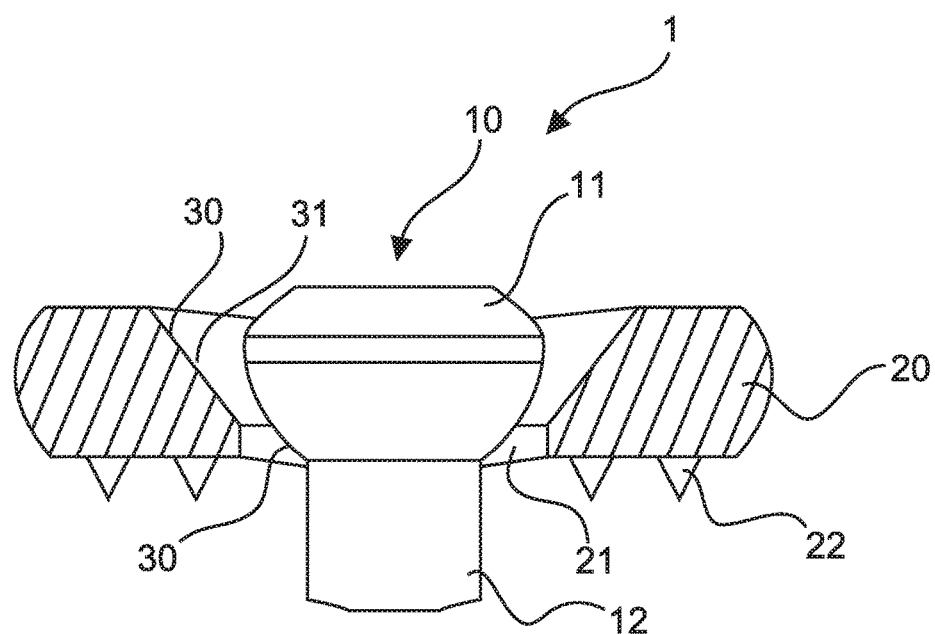
FIG. 1 shows a schematic drawing of an example of a bone screw system.
Figure 2:
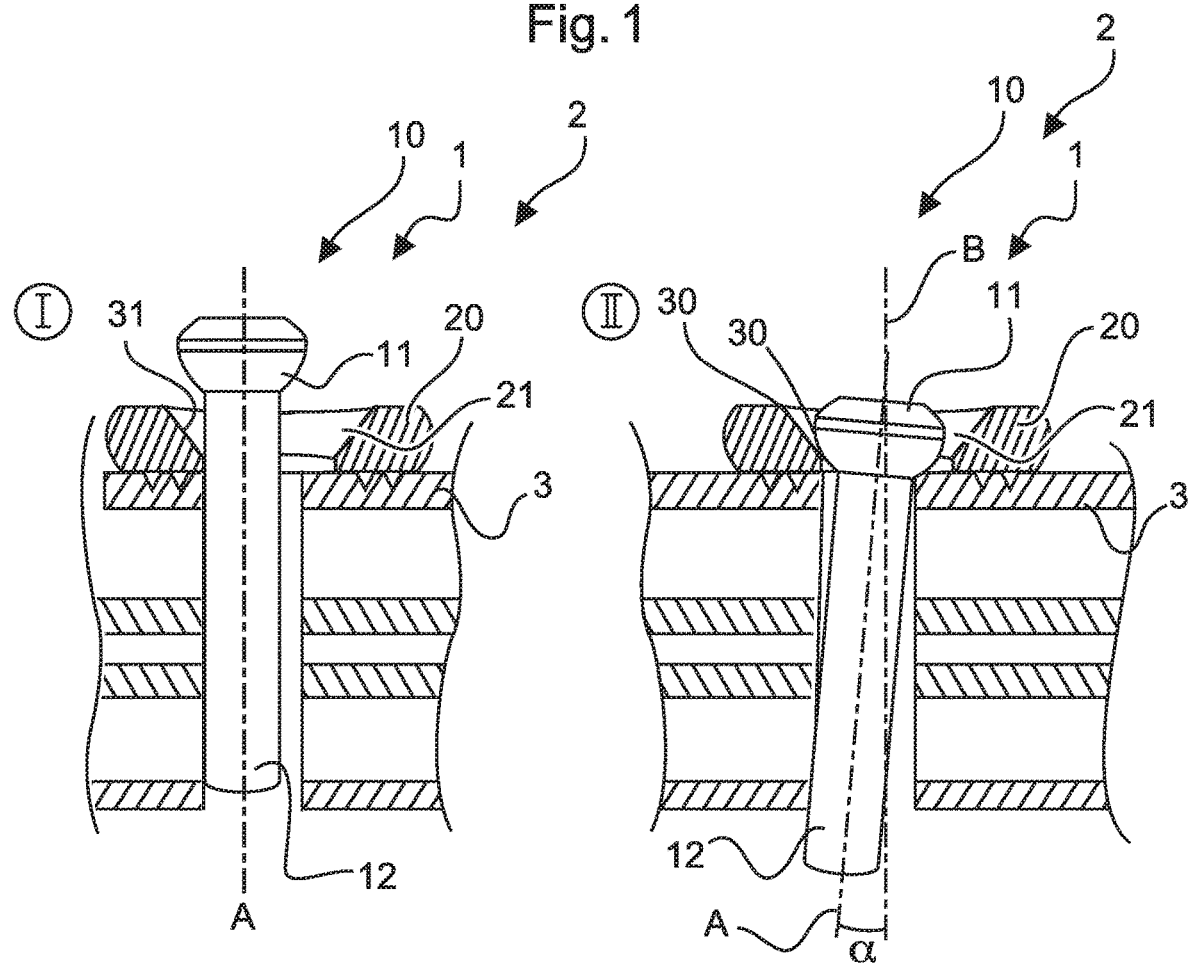
FIG. 2 shows a schematic drawing of an example of a bone screw system.

FIGS. 1 and 2 show schematically and exemplarily an embodiment of a bone screw system 1 according to the invention FIG. 2 shows schematically and exemplarily an embodiment of an implant system 2 according to the invention. The implant system 2 comprises the bone screw system 1 and an implant 3. The implant 3 is fixed to a bone by means of the bone screw system 1. The implant may be (part of) a plate, a nail, an intramedullary nail, a rod, a pin and the like. The bone screw system 1 can however also be used to be directly screwed into the bone without the implant.

The bone screw system 1 can be used for angularly locking a bone screw 10 into a bore. The bore is here provided in an implant. The implant bore is here a circular hole. The bone screw system 1 comprises a bone screw 10 and a washer 20. The screw 10 is here a standard bone screw. The screw 10 comprises a screw head 11 and a screw shaft 12. The washer 20 comprises a washer bore 21 without an internal thread.

A diameter of the washer bore 21 is larger than an outer diameter of the screw shaft 12. In this example, the diameter of the washer bore 21 is more than 20 percent larger than the outer diameter of the screw shaft 12. This size difference is larger than necessary for a simple passage of the screw shaft through the washer bore 21. This allows a displacement and in particular a lateral and not only longitudinal displacement of the screw shaft 12 within the washer bore 21. The diameter of the washer bore 21 is smaller than an outer diameter of the screw head 11. This prevents the screw head 11 from moving through the washer bore 21.

The screw 10 and the washer 20 comprise each an engagement portion for an engagement with each other. The engagement portion of the washer 20 comprises an inclined surface 31 and is in a cross section cone shaped. The inclined surface 31 is configured to force the screw shaft 12 sideward upon screwing in of the screw 10 so that a longitudinal axis A of the screw 10 is tilted relative to an axis B of the washer bore 21. The engagement portion of the screw 10 is curved and arranged as a transition between the screw shaft 12 and the screw head 11 and comprises an outer surface of a proximal shaft portion of the screw 10. The engagement portion of the washer 20 comprises an inner surface of the washer bore 21.

In other words, the inclined surface 31 forces the screw shaft 12 sideward upon screwing in of the screw 10 into the washer bore 21. The sideward movement of the screw shaft 12 leads to a tilt of the longitudinal screw axis and thereby of the screw 10 relative to the washer bore axis with an angle α. The angle α may be in a range of 10 to 45°. In other words, the screw 10 is inserted at a slight angle into the washer bore 21 and thereby provides a controlled angular deviation or offset between the screw axis A and the washer bore axis B. By this tilt, angle, deviation or offset, the screw 10 may be locked into or be interlocked with the washer bore 21. The longitudinal axis B of the washer bore is here parallel to a longitudinal axis of the bore in the implant. The axes of the washer bore and of the bore in the implant are here displaced to each other so that the axis B of the washer bore lies on a side wall of the bore in the implant.

As a result, the bone screw system 1 according to the invention can be used for interlocking the screw 10 and the washer bore 21.

The washer 20 comprises spikes as a fixing mechanism 22 on a bottom surface of the washer 20, wherein the spikes are configured for an engagement with a bone surface. The spikes or the fixing mechanism 22 firmly anchor the washer 20 and thereby the bone screw system 1 to the bone surface. This can be done before a final seating of the screw 10 and helps also after the final seating to hold to the bone screw system 1 to the bone surface.

Figure 3:
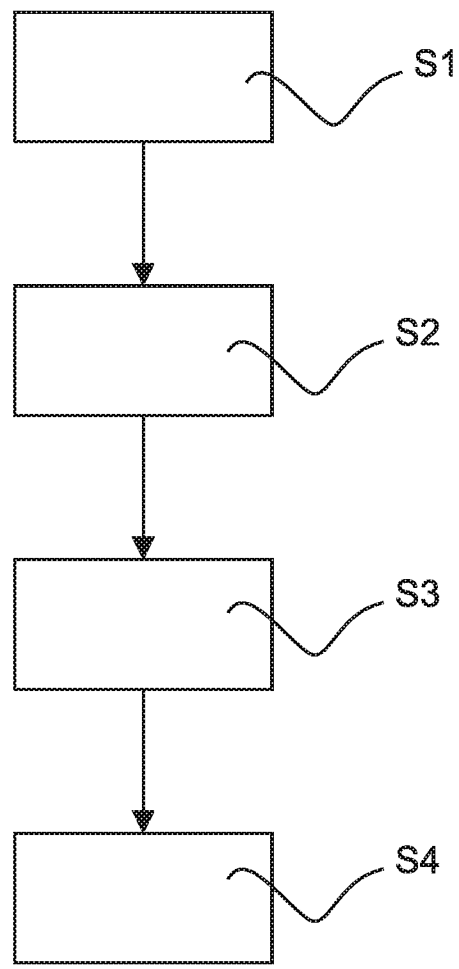
FIG. 3 shows basic steps of an example of a method of locking a bone screw system into a bore.

FIGS. 2 and 3 shows basic steps of an example of a method of locking a bone screw system 1 into a bore. The method of locking a bone screw system 1 into a bore comprises the following steps:

In a step S1), as shown in the left part of FIG. 2 under I, providing a screw system 1 as described above.

In a step S2), inserting a screw 10 of the screw system 1 into a washer 20 of the screw system 1.

In a step S3), screwing the screw 10 with a longitudinal screw axis A into the washer bore 21 with a longitudinal washer bore axis B. A distal shaft portion of the screw 10 is aligned with the longitudinal washer bore axis B.

In a step S4), as shown in the right part of FIG. 2 under II, engaging engagement portions of the screw 10 and the washer 20. At least one of the engagement portions comprise an inclined surface 31 so as to force the screw 10 sideward upon further screwing in of the screw 10 so that the screw axis A is tilted relative to the washer bore axis B.

In other words, the washer 20 is placed on the bore in an implant 3 provided on the bone. An inner edge of the washer bore 21 may be aligned with an inner edge of the bore in the implant 3. Thus, a central axis of the larger washer bore 21 is offset from a central axis of the implant bore. The washer 20 has spikes which fix the washer 20 at the implant 3. Then, the screw 10 is screwed in the fixed washer 20. When a head 11 of the screw 10 slides down the inclined surface 31 of the washer 20, the screw 10 tilts. Thereby, a user may adjust the offset between the washer bore 21 and the implant bore depending on how the screw needs to be tilted to produce the desired angle between the screw axis A and the washer bore axis B.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. The mere fact that certain measures are re-cited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone screw system comprising:
   a screw including a screw head and a screw shaft, and
   a washer including a washer bore,
   wherein the washer bore has a diameter larger than an outer diameter of the screw shaft allowing a sideward displacement of the screw shaft within the washer bore, and the diameter of the washer bore is smaller than an outer diameter of the screw head preventing the screw head from moving through the washer bore,
   wherein the screw has an outer surface that includes a first engagement portion and the washer bore has an inner surface that includes a second engagement portion for engagement with the first engagement portion, the first engagement portion having a first shape and the second engagement portion having a second shape different from the first shape, and
   wherein the second engagement portion comprises an inclined planar surface around an entire perimeter of the washer bore so as to force the screw shaft sideward upon screwing in of the screw so that a longitudinal axis (A) of the screw is tilted relative to a longitudinal axis (B) of the washer bore.

2. The bone screw system of claim 1, wherein the diameter of the washer bore is more than 10 percent larger than the outer diameter of the screw shaft.

3. The bone screw system of claim 2, wherein the diameter of the washer bore is more than 20 percent larger than the outer diameter of the screw shaft.

4. The bone screw system of claim 1, wherein the first engagement portion of the screw is arranged as a transition between the screw shaft and the screw head.

5. The bone screw system of claim 4, wherein the first engagement portion of the screw comprises an outer surface of a proximal shaft portion of the screw.

6. The bone screw system of claim 5, wherein the second engagement portion is cone shaped.

7. The bone screw system of claim 1, wherein the washer comprises a fastener on a bottom surface configured for an engagement with a bone surface.

8. The bone screw system of claim 7 wherein the fastener comprises spikes for engaging the bone surface.

9. The bone screw system of claim 8 wherein the first engagement portion on the screw is part-spherical and the second engagement portion on the washer is a conical recess extending inwardly towards a central axis of the washer bore on moving towards the washer bottom surface.

10. An implant system comprising:
    the bone screw system of claim 1, and
    an implant,
    wherein the implant is configured to be fixed to a bone by means of the bone screw system.

11. A method for locking a bone screw system, comprising the following steps:
    providing the bone screw system according to claim 1,
    inserting the screw of the bone screw system into the washer of the bone screw system,
    screwing the screw with the longitudinal screw axis (A) into the washer bore with the longitudinal washer bore axis (B), wherein a distal shaft portion of the screw is aligned with the washer bore axis (B), and
    engaging the first engagement portion of the screw with the second engagement portion of the washer, wherein the second engagement portion comprises the inclined planar surface around an entire perimeter of the washer bore so as to force the screw sideward upon further screwing in of the screw so that the longitudinal screw axis (A) is tilted relative to the washer bore axis (B).

12. The method of claim 11, wherein an outer surface of the screw is aligned with an inner edge of the washer bore prior to screwing the screw into the washer bore.

13. The method of claim 11, wherein a diameter of the washer bore is more than 20 percent larger than an outer diameter of the screw shaft.

14. The method of claim 12 wherein the washer is placed on a surface of a bone and held in a fixed position on the bone while the bone screw is screwed into the bone.

15. The method of claim 14 wherein the washer has a bone contacting surface comprising spikes for engaging the bone to fix the position of the washer.

16. The method of claim 11, wherein the screw is screwed into bone or into an implant mounted on or in the bone.

17. The bone screw system of claim 1, wherein the first engagement portion is located entirely on the screw head.

18. The bone screw system of claim 1, wherein the first engagement portion has a first surface area and the second engagement portion has a second surface area different from the first surface area.

19. A bone screw system comprising:
    a screw including a screw head and a screw shaft, and
    a washer including a washer bore,
    wherein the washer bore has a diameter larger than an outer diameter of the screw shaft allowing a sideward displacement of the screw shaft within the washer bore, the diameter of the washer bore being smaller than an outer diameter of the screw head thereby preventing the screw head from moving through the washer bore,
    wherein the screw head and the washer comprise engagement portions for an engagement with each other such that the screw is engageable with the washer in any one of a plurality of orientations relative to the washer, the engagement being through at least one point of contact or a line of contact between the screw head and the washer, wherein the engagement portion of the washer is located on an inclined surface around an entire perimeter of the washer bore so as to force the screw shaft sideward upon screwing in of the screw so that a first longitudinal axis of the screw is tilted relative to a second longitudinal axis of the washer bore, and wherein the plurality of orientations include a first orientation where the screw shaft is in a first plane and a second orientation where the screw shaft is in a second plane different from the first plane.

20. The bone screw system of claim 19, wherein the engagement portion of the washer includes a conical surface and the engagement portion of the screw head includes a partially spherical surface.

\* \* \* \* \*